US005629260A

United States Patent [19]
Utz et al.

[11] Patent Number: 5,629,260
[45] Date of Patent: May 13, 1997

[54] HETERIC EO/PO BLOCK COPOLYMERS AS ADJUVANTS FOR HERBICIDAL FORMULATIONS

[75] Inventors: Christopher G. Utz, Wyandotte, Mich.; Donald A. Poucher, Sparta, N.J.

[73] Assignee: BASF Corporation, Mount Olive, N.J.

[21] Appl. No.: 507,099

[22] Filed: Jul. 26, 1995

[51] Int. Cl.$^6$ .................................................. A01N 25/30
[52] U.S. Cl. ........................ 504/116; 504/247; 504/324
[58] Field of Search .................................. 504/116, 247, 504/324; 71/DIG. 1

[56] References Cited

U.S. PATENT DOCUMENTS

| | | | |
|---|---|---|---|
| 4,266,965 | 5/1981 | Simons | 71/118 |
| 4,931,080 | 6/1990 | Chan | 71/87 |
| 5,047,079 | 9/1991 | Djafar | 71/86 |
| 5,078,782 | 1/1992 | Nielsen et al. | 71/100 |
| 5,104,647 | 4/1992 | Policello | 514/772 |
| 5,187,191 | 2/1993 | Otten | 514/772.3 |

OTHER PUBLICATIONS

McWhorter, C. G. "The Physiological Effects of Adjuvants on Plants" Chapter 6 in *Weed Physiology: vol. II, Herbicide Physiology*, Stephen Ol Duke, ed. CRC Press. 1985. pp. 141–158.

Balneaves; The Effect of Added Surfactant on the performance of Scrubweed Herbicides; 98–101 Proc. 38th N. Z. Weed and Pest Control Conf. 1985.

*Primary Examiner*—S. Mark Clardy
*Attorney, Agent, or Firm*—Joanne P. Will

[57] ABSTRACT

The invention relates to the use of liquid heteric EO/PO, wherein EO is ethylene oxide and PO is propylene oxide, block copolymers, containing at least 30% by weight EO, as a tank mix adjuvant for enhancing the weed killing activity of herbicidal formulations.

7 Claims, No Drawings

HETERIC EO/PO BLOCK COPOLYMERS AS ADJUVANTS FOR HERBICIDAL FORMULATIONS

FIELD OF THE INVENTION

The invention relates to the use of liquid heteric EO/PO, wherein EO is ethylene oxide and PO is propylene oxide, block copolymers, containing at least 30% by weight EO, as a tank mix adjuvant for enhancing the weed controlling activity of herbicidal formulations.

BACKGROUND OF THE INVENTION

The use of surfactants as adjuvants for enhancing herbicide uptake is known. Detailed discussions of the use of surfactants in agrochemical formulations are described in *Surfactants in Agrochemicals*, Tharwat F. Tadros, Marcel Decker, Inc. Surfactant Science Series, 1995 and *Adjuvants for Herbicides*, Weed Science Society of America, 1982, both publications incorporated by reference herein.

Further, U.S. Pat. No. 4,931,080, issued Jun. 5, 1990 to Chan and U.S. Pat. No. 5,047,079, issued Sep. 10, 1991 to Djafar et al, both disclose solid weed killing compositions comprising N-phos-phonomethyl-N-carboxymethyl herbicides and nonionic surfactants such as PLURONIC® surfactants which are EO/PO block copolymers. In U.S. Pat. No. 5,104,647, issued Apr. 14, 1992, Policello discloses a surfactant blend comprising an organosilicone compound and a polyalkylene oxide copolymer, such as PLURONIC® surfactant, useful as an agricultural adjuvant. Finally, U.S. Pat. No. 5,187,191, issued Feb. 16, 1993 to Otten et al, discloses physically stable aqueous pesticide compositions comprising water insoluble pesticides, polyoxyalkylene copolymer and water. Said polyoxyalkylene copolymer is heteric, i.e. it is comprised of EO and PO units, wherein some PO is incorporated into the EO blocks, e.g. (EO/PO)(PO)(EO/PO), in order to provide a liquid surfactant which is more easily used than a paste.

However, the use of these liquid heteric EO/PO block copolymers as adjuvants to increase the uptake of herbicides has not been described. Prior to the invention described herein, non-heteric EO/PO blocks with higher amounts of EO (i.e. >30%) had not been previously tested in tank mixes because their physical form (paste) rendered them impractical for this application.

Applicants have now surprisingly discovered that liquid heteric EO/PO block copolymers, wherein the EO content is at least 30% by weight, are useful for enhancing the efficacy of herbicides and, thus, enhancing weed controlling activity.

SUMMARY

A method of enhancing the weed controlling activity of a broad spectrum herbicide comprising the administration of said broad-spectrum herbicide wherein a heteric EO/PO copolymer is used in conjunction with said broad-spectrum herbicide and said heteric EO/PO copolymer has surface active properties, and the formula:

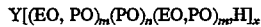

wherein Y is the nucleus of an organic reactive hydrogen compound having x reactive hydrogen atoms and up to 6 carbon atoms, x is an integer, EO is ethylene oxide, PO is a propylene oxide hydrophobe having an oxygen/carbon ratio of not more than 0.40, (EO,PO) represents a hydrophilic heteric block (a block of EO with PO molecules interspersed) having an oxygen/carbon ratio of more than 0.40, m, m' and n are numbers such that the total molecular weight of said hydrophilic heteric block is from about 660 to 11,400, the total molecular weight of said PO hydrophobe is from about 1500 to 3600 and the total molecular weight of said copolymer ranges from about 2200 to 15,000, said copolymer being at least 30 weight percent hydrophilic (weight of the hydrophilic block) with said hydrophilic heteric block comprising from about 5 to 40 weight percent of PO;

DETAILED DESCRIPTION

The present invention relates to a method of enhancing the systemic weed controlling activity of a broad spectrum herbicide comprising the administration of said broad-spectrum herbicide wherein a heteric EO/PO copolymer is used in conjunction with said broad-spectrum herbicide and said heteric EO/PO copolymer has surface active properties, and the formula:

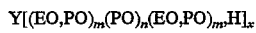

wherein Y is the nucleus of an organic reactive hydrogen compound having x reactive hydrogen atoms and up to 6 carbon atoms, x is an integer, EO is ethylene oxide, PO is a propylene oxide hydrophobe having an oxygen/carbon ratio of not more than 0.40, (EO,PO) represents a hydrophilic heteric block having an oxygen/carbon ratio of more than 0.40, m, m' and n are numbers such that the total molecular weight of said hydrophilic heteric block is from about 660 to 11,400, the total molecular weight of said PO hydrophobe is from about 1500 to 3600 and the total molecular weight of said copolymer ranges from about 2,200 to 15,000, said copolymer being at least 30 weight percent hydrophilic with said hydrophilic heteric block comprising from about 5 to 40 weight percent of PO;

THE BROAD SPECTRUM HERBICIDE

Broad spectrum herbicides useful in the practice of the present invention include, but are not limited to, bentazone, (3-isopropyl-1H-2,1,3-benzothiadiazen-4(3H)-one-2,2-dioxide); quinchlorac, (3,7-dichloro-8-quinolinecarboxylic acid); acifluorfen, (sodium 5-[2-chloro-4-trifluoroethyl] phenoxy]2-nitrobenzoate); sethoxydim, (2-[1-(ethoxyimino)butyl]-5-[2 ethylthio)propyl]-3-hydroxy-2-cyclohexen-1-one); and glyphosate, (isopropylamine salt of N-(phosphono-methyl) glycine). Most preferred are quinchlorac and acifluorfen.

THE EO/PO POLYMERS

Liquid heteric EO/PO copolymers having surface active properties, useful in the practice of the present invention have the formula:

wherein Y is the nucleus of an organic reactive hydrogen compound having x reactive hydrogen atoms and up to 6 carbon atoms, x is an integer, EO is ethylene oxide, PO is a propylene oxide hydrophobe having an oxygen/carbon ratio of not more than 0.40, (EO,PO) represents a hydrophilic heteric block having an oxygen/carbon ratio of more than 0.40, m,m' and n are numbers such that the total molecular weight of said hydrophilic heteric block is from about 660 to 11,400, the total molecular weight of said PO hydrophobe is from about 1500 to 3600 and the total molecular weight of said copolymer ranges from about 2,200 to 15,000, said copolymer being at least 30 weight percent hydrophilic with said hydrophilic heteric block comprising from about 5 to 40 weight percent of PO;

The liquid heteric EO/PO polymers useful in the compositions of the present invention are described in detail in U.S. Pat. No. 5,187,191, incorporated by reference herein.

Preferred heteric EO/PO polymers useful in the compositions of the present invention are those with a PO block of at least 2400 molecular weight and between 30–60% EO. The heteric EO/PO polymers preferred in the practice of the present invention are commercially available as PLURAFLO® L860 (a 2400 molecular weight PO block with 60% EO, i.e., 60% by weight hydrophilic); PLURAFLO® L1030 (a 3000 molecular weight PO block with 30% EO, i.e., 30% by weight hydrophilic) and PLURAFLO® L1060 (a 3000 molecular weight PO block with 60% EO, i.e., 60% by weight hydrophilic), from the BASF Corporation, Mt. Olive, N.J.

TESTING OF THE COMPOSITIONS USEFUL IN THE METHOD OF THE PRESENT INVENTION

PLURAFLO L860, PLURAFLO L1030, and PLURAFLO L1060 were applied as surfactants with Poast® (sethoxydim—0.11 kg active ingredient/hectare (ai/ha), Basagran® (bentazone—0.56 kg active ingredient/hectare (ai/ha), Blazer® (acifluorfen—0.28 kg active ingredient/ hectare (ai/ha), and Facet® (quinchlorac—0.14 kg active ingredient/hectare (ai/ha) (all products available from BASF Corporation, Mount Olive, N.J.). The PLURAFLO materials were added at 4.6, 2.3, 1.17 liter/hectare (1/ha). Treatments were applied in the laboratory with a laboratory track sprayer at 187 L/Ha and 276 Kpa (20 GPA, 40 psi). Bentazone and acifluorfen applications were made to soybeans with yellow nutsedge (*Cyperus esculentus*), prickly sida (*Sida spinosa*), velvet leaf (*Abutilon theophrasti*), redroot pigweed (*Amaranthus retroflexus*) and tall morning glories (ipomoea hederacea) and giant foxtail. Sethoxydim and quinchlorac were applied to soybeans, rice, barnyard grass (*Echinochloa crus-galli*), giant foxtail (*Setaria faberii*), large crabgrass (*Digitaria sanguinalis*), corn, shattercane (*Sorghum vulgare*), green sprangletop (*Leptochloa dubia*), broadleaf signalgrass (*Bracharia platyphylla*), and green foxtail (*Setaria viridis*), hempsesbania; and ladysthumb (*Polygonum persicaria*). In all trials the broadleaf weeds had four to six true leaves and grasses had three to four leaves. Weeds were generally larger in stature than plants grown outdoors having the same number of leaves. All plants were grown in an organic planting medium, Metro Mix 360 and fertilized with Osmocote slow release fertilizer.

The treatments described herein can also be prepared in the field as tank mixes according to methods known to those skilled in the art.

Tables 1 & 2 show the results of the testing of the liquid heteric EO/PO polymers in enhancing quinchlorac and acifluorfen activity.

Specifically, in Table 1, the efficacy of the quinchlorac active as a weed controller is enhanced by the use of the EO/PO heteric copolymers, PLURAFLO L860, PLURAFLO L1030, PLURAFLO L1060, especially in controlling barnyard grass, when compared to the untreated control. Quinchlorac is a systemic rice herbicide and barnyard grass comprises up to 80% of the weed problems in the crops. Further, the use of these EO/PO heteric copolymers is more effective in enhancing barnyard grass control than a crop oil concentrate (COC).

The use of EO/PO heteric copolymers as adjuvants also enhances the weed killing effectiveness of quinchlorac on green foxtail and hempsesbania.

In Table 2, the efficacy of the contact herbicide acifluorfen as a weed controller is enhanced by the use of EO/PO heteric copolymers, particularly PLURAFLO L1030 and L1060, in tall morning glories and giant foxtail when compared to the untreated control. Further, the use of these EO/PO heteric copolymers is more effective in enhancing foxtail control than the COC.

Further, in both sets of data (Tables 1 & 2), while the weeds are controlled, the rice is completely unharmed and soybean injury is minimal. The data also illustrate that the quinchlorac and acifluorfen can be applied at lower rates, i.e., the effectiveness at 1.17 l/ha can be just as effective or superior to applications at 2.3 l/ha and 4.6 l/ha. Thus, while the EO/PO heteric block copolymers enhance the systemic uptake or the contact area of these broad spectrum herbicides, there is no increase in injury to the cash crop.

TABLE 1

Effects of Surfactants on Quinchlorac Efficacy

| TREATMENT | L/HA | SOYBEANS | RICE | BARNYARD GRASS | GIANT FOXTAIL | LARGE CRABGRASS | VOLUNTEER CORN | SORGHU | SPRANGLETOP | SIGNAL GRASS | GREEN FOXTAIL | HEMP SESBANIA | VELVET LEAF |
|---|---|---|---|---|---|---|---|---|---|---|---|---|---|
| Untreated | | 0 | 0 | 0 | 0 | 0 | 0 | 0 | 0 | 0 | 0 | 0 | 0 |
| Quinchlorac | | 10 | 0 | 0 | 0 | 0 | 0 | 0 | 0 | 0 | 0 | 0 | 0 |
| Crop Oil Concentrate | | 5 | 0 | 38 | 10 | 0 | 0 | 0 | 0 | 10 | 78 | 75 | 41 |
| PLURAFLO L860 | 4.6 | 4 | 0 | 73 | 10 | 0 | 0 | 0 | 5 | 10 | 75 | 75 | 45 |
| | 2.3 | 5 | 0 | 75 | 10 | 0 | 0 | 0 | 10 | 10 | 20 | 25 | 31 |
| | 1.17 | 15 | 0 | 75 | 10 | 5 | 0 | 0 | 10 | 10 | 65 | 50 | 41 |
| PLURAFLO L1030 | 4.6 | 10 | 0 | 78 | 10 | 25 | 0 | 0 | 5 | 10 | 65 | 35 | 41 |
| | 2.3 | 5 | 0 | 73 | 10 | 25 | 0 | 0 | 5 | 10 | 75 | 25 | 42 |
| | 1.17 | 10 | 0 | 73 | 20 | 10 | 0 | 0 | 15 | 50 | 80 | 50 | 51 |
| PLURAFLO L1060 | 4.6 | 15 | 0 | 65 | 20 | 15 | 0 | 0 | 15 | 20 | 50 | 50 | 42 |
| | 2.3 | 15 | 0 | 75 | 20 | 25 | 0 | 0 | 10 | 20 | 65 | 65 | 49 |
| | 1.17 | 10 | 0 | 75 | 20 | 15 | 0 | 0 | 15 | 20 | 50 | 50 | 44 |

TABLE 2

| | | | | | RED- | | | | | MORN- |
| | | | VEL- | ROOT | | YELLOW | | GIANT | ING |
| | SOY- | COCKLE- | VET | PIG- | PRICKLY | NUTS- | LADYS- | FOX- | |
| TREATMENT | L/HA | BEANS | BUR | LEAF | WEED | SIDA | EDGE | THUMB | TAIL | GLORIES |
|---|---|---|---|---|---|---|---|---|---|---|
| Untreated | | 0 | 0 | 0 | 0 | 0 | 0 | 0 | 0 | 0 |
| Acifluorfen | | 5 | 90 | 63 | 98 | 20 | 18 | 70 | 88 | 20 |
| Crop Oil Concentrate | | 7 | 65 | 63 | 98 | 10 | 15 | 85 | 75 | 10 |
| PLURAFLO L860 | 4.6 | 7 | 30 | 75 | 100 | 20 | 90 | 95 | 95 | 20 |
| | 2.3 | 7 | 83 | 65 | 100 | 20 | 10 | 75 | 99 | 20 |
| | 1.17 | 7 | 75 | 75 | 100 | 15 | 10 | 75 | 100 | 15 |
| PLURAFLO L1030 | 4.6 | 7 | 63 | 30 | 100 | 38 | 25 | 90 | 93 | 38 |
| | 2.3 | 7 | 63 | 50 | 100 | 45 | 28 | 80 | 97 | 100 |
| | 1.17 | 7 | 100 | 100 | 100 | 35 | 20 | 90 | 90 | 95 |
| PLURAFLO L1060 | 4.6 | 7 | 93 | 93 | 100 | 25 | 25 | 85 | 96 | 100 |
| | 2.3 | 7 | 100 | 30 | 100 | 20 | 35 | 78 | 95 | 100 |
| | 1.17 | 7 | 63 | 45 | 100 | 20 | 25 | 75 | 98 | 100 |

We claim:

1. A method of enhancing the weed controlling activity of a broad spectrum herbicide comprising the administration of said broad-spectrum herbicide wherein a heteric EO/PO copolymer is used in conjunction with said broad-spectrum herbicide and said heteric EO/PO co-polymer has surface active properties, and the formula:

$$Y[(EO,PO)_m(PO)_n(EO,PO)_{m'}H]_x$$

wherein Y is the nucleus of an organic reactive hydrogen compound having x reactive hydrogen atoms and up to 6 carbon atoms, x is an integer, EO is ethylene oxide, PO is a propylene oxide hydrophobe having an oxygen/carbon ratio of not more than 0.40, (EO,PO) represents a hydrophilic heteric block having an oxygen/carbon ratio of more than 0.40, m,m' and n are numbers such that the total molecular weight of said hydrophilic heteric block is from about 660 to 11,400, the total molecular weight of said PO hydrophobe is from about 1500 to 3600 and the total molecular weight of said copolymer ranges from about 2,200 to 15,000 said copolymer being at least 30 weight percent hydrophilic with said hydrophilic heteric block comprising from about 5 to 40 weight percent of PO.

2. A method according to claim 1, wherein, said broad spectrum herbicide is quinchlorac; said heteric EO/PO copolymer has a PO-block molecular weight of 2400 and is 60% by weight hydrophilic.

3. A method according to claim 1, wherein said broad spectrum herbicide is quinchlorac; said heteric EO/PO copolymer has a PO-block molecular weight of 3000 and is 30% by weight hydrophilic.

4. A method according to claim 1, wherein said broad spectrum herbicide is quinchlorac; said heteric EO/PO copolymer has a PO-block molecular weight of 3000 and is 60% by weight hydrophilic.

5. A method according to claim 1, wherein said broad spectrum herbicide is acifluorfen; said heteric EO/PO copolymer has a PO-block molecular weight of 3000 and is 60% by weight hydrophilic.

6. A method according to claim 1, wherein said broad-spectrum herbicide is acifluorfen; said beteric EO/PO copolymer has a PO-block molecular weight of 3000 and is 30% by weight hydrophilic.

7. A method according to claim 1, wherein said broad-spectrum herbicide is acifluorfen; said heteric EO/PO copolymer has a PO-block molecular weight of 3000 and is 60% by weight hydrophilic.

* * * * *